United States Patent [19]

Ryder et al.

[11] Patent Number: 4,863,698
[45] Date of Patent: Sep. 5, 1989

[54] DISINFECTOR FOR GLASS VIALS

[75] Inventors: Francis E. Ryder, Arab; Donald E. Johnson, Joppa; Gerald L. Krupp, Huntsville, all of Ala.

[73] Assignee: Ryder International Corporation, Arab, Ala.

[21] Appl. No.: 100,406

[22] Filed: Sep. 24, 1987

[51] Int. Cl.⁴ ............................................. G01B 11/00
[52] U.S. Cl. .................................... 422/116; 219/492; 219/493; 219/505; 219/506; 219/531; 422/108
[58] Field of Search ............. 219/492, 493, 506, 518, 219/505, 524, 531; 422/116, 118, 108

[56] References Cited

U.S. PATENT DOCUMENTS

| | | | |
|---|---|---|---|
| 3,093,449 | 6/1963 | Kotarski et al. | 422/112 |
| 3,801,278 | 4/1974 | Wagner et al. | 422/116 |
| 4,002,924 | 1/1977 | Busch | 219/505 X |
| 4,013,410 | 3/1977 | Thomas et al. | 21/58 |
| 4,165,359 | 8/1979 | Thomas et al. | 422/105 |
| 4,228,136 | 10/1980 | Thomas | 422/307 |
| 4,235,842 | 11/1980 | Thomas et al. | 422/116 |
| 4,242,304 | 12/1980 | Ryder | 422/119 |
| 4,242,572 | 12/1980 | Thomas et al. | 219/521 |
| 4,243,632 | 1/1981 | Ryder | 422/119 |
| 4,251,719 | 2/1981 | Ryder | 219/521 |
| 4,256,952 | 3/1981 | Thomas et al. | 219/521 |
| 4,261,950 | 4/1981 | Bainbridge et al. | 422/116 X |
| 4,302,664 | 11/1981 | Ryder et al. | 219/504 |
| 4,303,828 | 12/1981 | Thomas et al. | 219/521 |
| 4,307,289 | 12/1981 | Thomas et al. | 219/521 |
| 4,331,859 | 5/1982 | Thomas et al. | 219/521 |
| 4,388,521 | 6/1983 | Thomas et al. | 219/521 |
| 4,441,769 | 4/1984 | Thomas et al. | 312/270 |
| 4,492,854 | 1/1985 | Ryder et al. | 219/521 |
| 4,518,850 | 5/1985 | Grasso | 219/505 |
| 4,607,154 | 8/1986 | Mills | 219/505 |
| 4,659,911 | 4/1987 | Ryder et al. | 219/521 |
| 4,699,738 | 10/1987 | De Petris | 219/511 X |

OTHER PUBLICATIONS

Webster's II, New Riverside University Dictionary, The Riverside Publishing Co., 1984.

Primary Examiner—Barry S. Richman
Assistant Examiner—Amalia L. Santiago
Attorney, Agent, or Firm—R. A. Giangiorgi

[57] ABSTRACT

A multiple station disinfector apparatus simultaneously heats a plurality of devices such as contact lenses. Each of these devices is disposed in a quantity of liquid within a closed container. The apparatus comprises a housing having a base portion and a recloseable cover portion and a plurality of similar recessed receptacles in the base for receiving the containers. Each receptacle has a bottom wall and sidewall of complementary shape for surroundingly engaging a bottom wall part and a substantial portion of a sidewall part of one of the containers. Heating elements are disposed for heating the receptacles. The bottom wall and side wall of each receptacle are disposed at a predetermined angular offset relative to vertical and horizontal directions when the base portion is resting on a horizontal surface, to thereby hold each of the containers at a corresponding angular offset for facilitating heat transfer from the heating elements to the liquid in each container through both the bottom wall and a substantial portion of the side wall of the container. A control circuit controls a predetermined cycle of heating effected by the heating elements.

16 Claims, 3 Drawing Sheets

DISINFECTOR FOR GLASS VIALS

BACKGROUND OF THE INVENTION

The present invention is directed to apparatus for disinfecting contact lenses, and more particularly to a disinfector apparatus, and more particularly still to a multiple station disinfector apparatus for effecting simultaneously the disinfection by heating of objects or devices held within a plurality of containers.

While the disinfector apparatus in accordance with the invention may find use for heat disinfecting over a broad range of applications, the description will be facilitated hereinbelow by specific reference to the problem of the disinfection of contact lenses. In particular, the soft or hydrophilic type of contact lenses must be disinfected by heating to assure destruction of bacteria. While heating devices for disinfecting individual pairs of lenses are generally known, one object of this invention is to provide a simple and reliable apparatus for simultaneously disinfecting a plurality of contact lenses. Such an apparatus is particularly useful in the fitting room of the eye care specialist wherein it is often desirable to have on hand a plurality of sample soft contact lenses for fitting purposes. In the lens fitting room, the soft contact lenses are interchanged to determine the proper fit for the patient. Accordingly, it is necessary to properly disinfect the sample lenses between such uses in fitting.

Heretofore, the only known means of disinfecting multiple lenses has been a sterilization process which requires the use of specialized bottles and a specialized capping process, not generally well-suited to the fitting room enviornment. Preferably, the disinfection is carried out with the soft contact lens disposed in a quantity of fluid within a suitable container, such as a glass vial or bottle-like container with a removable cap or closure. One problem encountered with the use of such glass vials or bottles is maintaining sufficient heat transfer from a heating element to the bottle to maintain the liquid therein at a proper temperature for assuring proper disinfection. Additionally, it is important to assure that the proper temperature is maintained for an adequate amount of time to assure disinfection.

Moreover, it is important to minimize the possibility of operator error by assuring correct time and temperature cycling of the disinfecting operation with minimal operator input. Ideally, suitable indicators should be provided to confirm to the operator that the process has been properly completed, to safeguard against interruptions in the process either by the operator or as a result of a power failure or the like.

OBJECTS AND SUMMARY OF THE INVENTION

Accordingly, it is a general object of the invention to provide a novel and improved professional disinfector for glass vials which overcomes the foregoing problems and provides the above-noted desirable features and advantages.

The invention provides a multiple station disinfector apparatus for simultaneously heating a plurality of devices such as contact lenses, each of said plurality of devices being disposed in a quantity of liquid within a closed container, said apparatus comprising: a housing comprising a base portion and a recloseable cover portion; well means disposed in said base portion and defining a plurality of similar recessed receptacles, each for receiving one of said containers therein; each said receptacle having a bottom wall and sidewall of complementary shape for surroundingly engaging a bottom wall part and a substantial portion of a sidewall part of one of said containers; heating means disposed for heating said receptacles; said bottom wall and said side wall of each said receptacle being disposed at a predetermined angular offset relative to vertical and horizontal directions when said base portion is resting on a horizontal surface, to thereby hold each of said containers at a corresponding angular offset for facilitating heat transfer from said heating means to the liquid in each said container through both said bottom wall and said substantial portion of said side wall of the container; and control circuit means for controlling a predetermined cycle of heating effected by said heating means.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

DETAILED DESCRIPTION OF THE ILLUSTRATED EMBODIMENT

Figure 1:
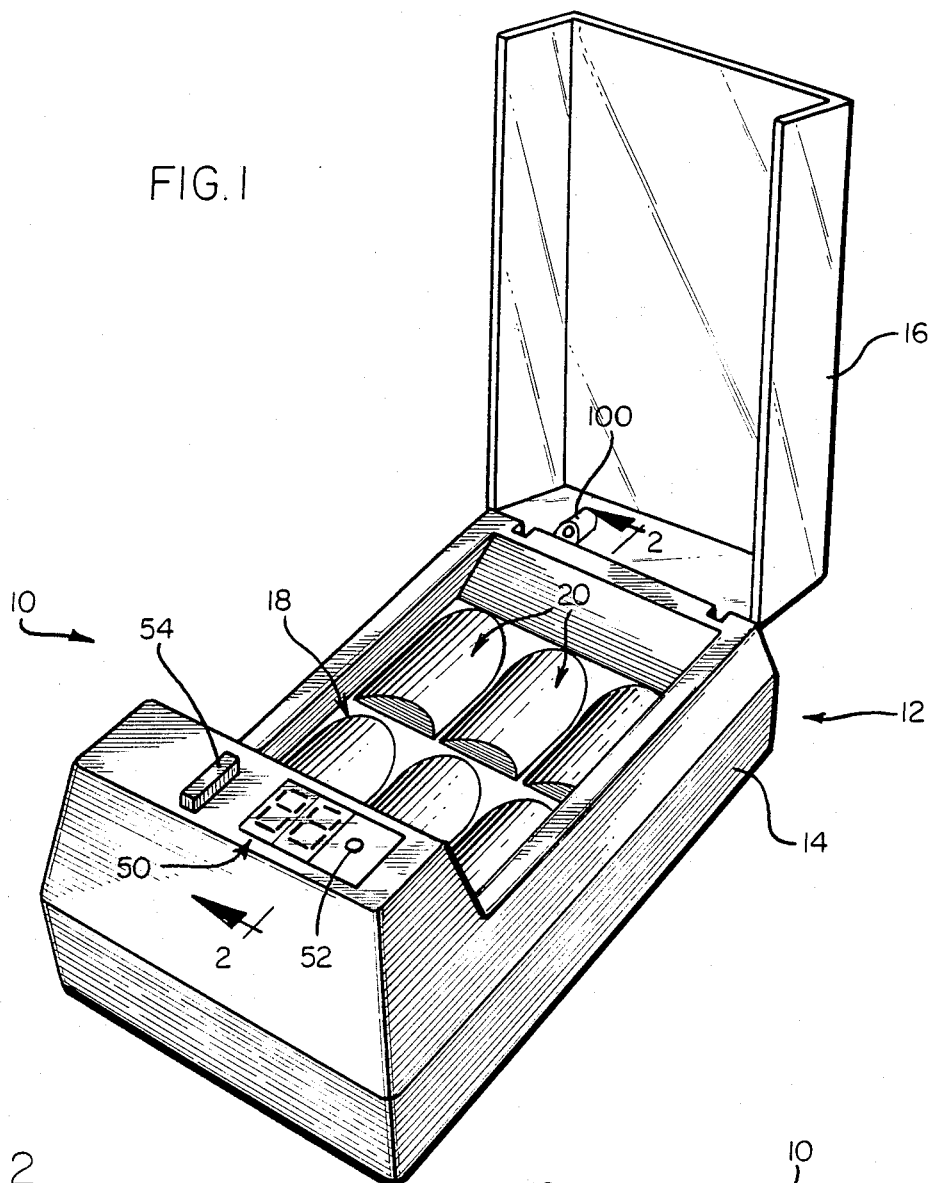
FIG. 1 is a top and front perspective view of a disinfector apparatus in accordance with the invention.
Figure 2:
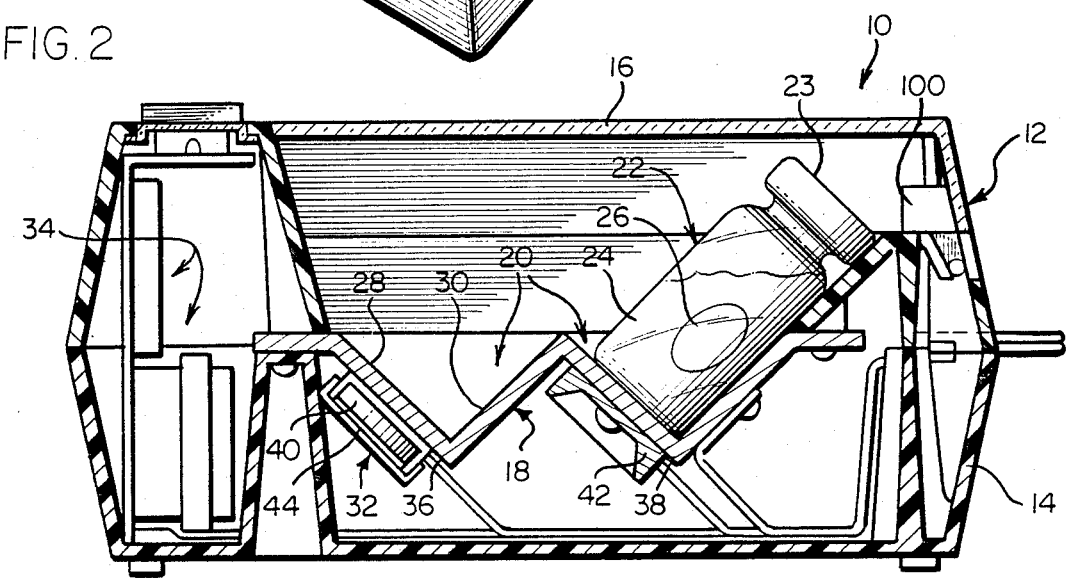
FIG. 2 is an enlarged sectional view taken generally along the line 2—2 of FIG. 1.

Referring to the drawings, and initially to FIGS. 1 and 2, a disinfector apparatus in accordance with the invention is designated generally by the reference numeral 10. The apparatus 10 includes a housing 12 comprising a base portion 14 and a reclosable cover portion 16. Preferably the cover portion 16 is hingedly coupled to the base portion 14 for movement between an open position as illustrated in FIG. 1 and a closed position as illustrated in FIG. 2. A well member or well means 18 is mounted or disposed in the base portion 14 and defines a plurality of similar recessed receptacles 20. In the illustrated embodiment these receptacles 20 are six in number. However, fewer or more such receptacles may be provided without departing from the invention.

In accordance with the invention, each of the receptacles 20 is of complementary configuration for surroundingly engaging a substantial outer surface portion of a glass vial or container 22. These glass vials or containers preferably are provided with suitable closures such as reusable caps 23 and are filled with a quantity of sterile fluid 24 for effecting disinfection by heating of a contact lens 26 disposed within the fluid 24.

In the illustrated embodiment, the containers 22 are substantially cylindrical. Accordingly, each of the receptacles 20 defines a generally circular bottom wall 28 and a semi-cylindrical sidewall 30 which is formed generally at right angles to bottom wall 28. The respective bottom walls 28 and side walls 30 are further formed at an angle or angular offset relative to horizontal and vertical planes, that is, with the base 14 disposed on a substantially horizontal surface. In the illustrated embodiment, this angle or angular offset is on the order of substantially 45 degrees. Accordingly, each semi-cylindrical sidewall portion 30 surroundingly engages a substantial portion of the corresponding sidewall of a generally cylindrical container 22.

It will be noted that the level of fluid 24 is such as to not quite fill the container 22. Hence, upon disposition of the container in the relatively angularly oriented receptacles 20, the configuration and angle of the receptacles results in surrounding engagement of that portion of the container 22 in which approximately 50 percent or more of the fluid or liquid 24 is disposed. Accordingly, heat transfer to the fluid 24 is substantially facilitated and optimized by the foregoing complementary shape and angular orientation of the receptacles 20.

Moreover, this angular orientation of receptacles 20 relative to the base 14 is such that the individual containers and their contents may be readily viewed when in place in the receptacles, without necessitating removal, for identification, of each container and the contact lens disposed therewithin. In this regard, the lid 16 is preferably of a transparent material to permit viewing of the containers therethrough. The above-described advantageous configuration of the receptacles 20 further permits the overall size of the apparatus 12 to be minimized so as to conveniently fit within limited space, for example, in a relatively small area, such as on a fitting table or counter for convenient use in fitting lenses to a patient.

Further in accordance with a preferred form of the invention, the material of the well 18, and hence of the receptacles 20, is preferably a heat sinking type of material to further facilitate the efficient transfer of heat to the respective containers 22 when disposed within the receptacles 20. Cooperatively, the invention further provides heating means designated generally by the reference numeral 32 for applying heat energy to the receptacles, and a novel control circuit means 34 for controlling the operation of the heating means 32. The control circuit 34 operates for applying heat energy to the receptacles for a predetermined duration of time to effect a disinfecting heating cycle of a predetermined, desired length.

In the preferred embodiment illustrated, the receptacles are further oriented in two rows in a side-by-side array, such that the bottoms 28 of each row are generally aligned in a co-planar arrangement. Accordingly, the bottoms of the receptacles 28 form a corresponding pair of generally planar undersurfaces 36, 38 in the illustrated embodiment. Advantageously, the heating means 32 are mounted to these generally planar undersurfaces 36, 38 so as to provide heat energy simultaneously to the aligned bottom portions 28 of the receptacles in the respective rows. In the illustrated embodiment, three of the receptacles 20 are aligned in each of the two rows; however, other arrangements may be selected without departing from the invention.

Preferably, the heating means include positive temperature coefficient (PTC) type heating elements, one of which is indicated by reference numeral 40 in FIG. 2. To facilitate and simplify the illustration, further PTC heating elements have been eliminated from the view of FIG. 2, being understood that at least one such element is associated with each of the undersurfaces 36, 38. Preferably, the heating elements are mounted to these surfaces 36, 38 by elongate brackets or bracket means such as bracket 42 which extends along each of the respective undersurfaces 36 and 38. As shown in FIG. 2, the brackets 42 are constructed of a metallic material and are of substantial thickness relative to the thickness of surfaces 36, 38, for example, such that the extension of the brackets along these undersurfaces will tend to facilitate substantially even heat distribution to the receptacles aligned in each row. Additionally, each heating element, such as element 40, is preferably enclosed in a quantity of insulation material 44 to substantially confine the heat energy transfer therefrom to the receptacles 20 and minimize the transmission of heat energy to other portions of the apparatus.

The apparatus 12 preferably includes relatively simple and easy to use control and display facilities, including of a two-digit display panel 50, a "ready" light 52 and a "start" push button 54. The operation of the start push button, ready light and two-digit display will be explained further hereinbelow in connection with the description of the control circuit of the invention.

Figure 3A:
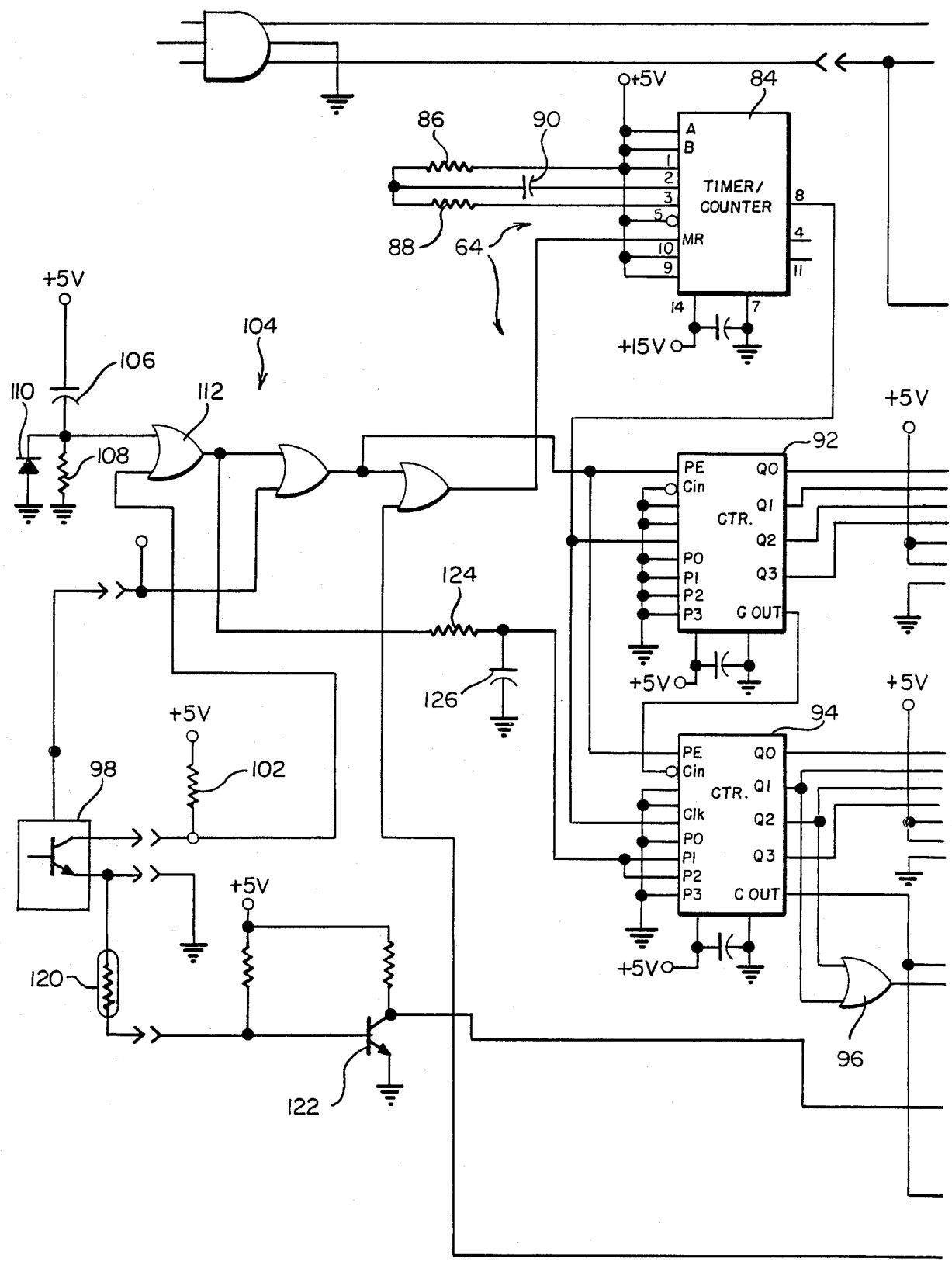
FIGS. 3A and 3B, taken together, form a schematic circuit diagram of a control circuit in accordance with a preferred form of the invention.
Figure 3B:
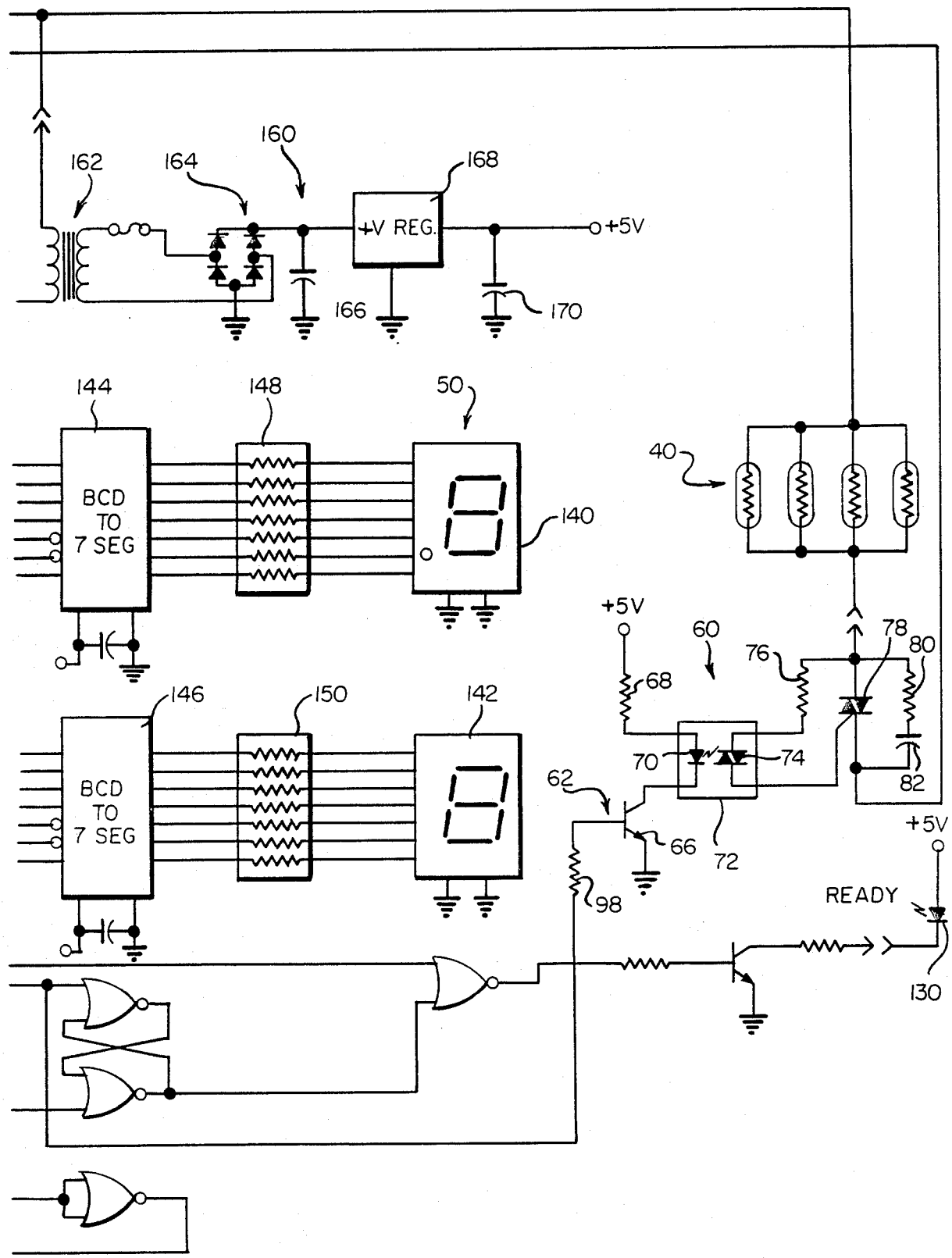

Turning now to FIGS. 3A and 3B, a preferred form of control circuit for the invention is illustrated in circuit schematic form. Referring initially to FIG. 3B, the heating or PTC elements 40 will be seen to be four in number, and these are preferably substantially symmetrically arrayed with respect to the undersurfaces 36, 38 of the receptacles 20 described above with reference to FIG. 2. In operation, a source of electrical energy, and preferably a 110 volt AC line, is selectively coupled for engergizing the heating elements 40 by way of a controllable switching circuit means designated generally by the reference numeral 60. The switching circuit 60 is coupled intermediate the heating elements and the neutral side of the AC circuit for selectively completing the AC power circuit with the heating elements 40.

The switching circuit 60 includes a control input 62 responsive to a predetermined control signal for making and breaking the circuit to the PTC heating elements 40. Moreover, a timing circuit means 64 is operatively coupled with the control input 62 for producing the necessary control signal for causing energization of the heating means or elements 40 for a predetermined time interval or duration.

Turning now in further detail to the switching circuit 60, it will be seen that a logic one or high level signal at control input 62 "turns on" the base of a transistor 66 causing the same to sink current from a positive supply through a current limiting resistor 68 and a light emitting diode (LED) 70. The LED 70 forms a part of an optically coupled triac driver circuit 72, preferably of the type MOC 3010. The other portion of this circuit comprises a light-sensitive triac element 74 which conducts in response to light emitted from LED 70. With triac 74 in a conducting state, AC current flows through a current limiting resistor and the triac 74 to the control or gate electrode of a power triac 78. A current snubbing network is also coupled in parallel with triac 78 and consists of a series coupled combination of a resistor 80 and a capacitor 82, to suppress switching transients that occur from the switching of triac 78 when the AC line voltage is not exactly at the zero crossing point.

Referring to FIG. 3A, the timer circuit 64 includes a timer/counter or oscillator/counter integrated circuit component 84, preferably of the type generally designated MC 14541B. Counter select pins are set high so that the counter 84 essentially divides by 65,536. The time constant is set by the selection of the RC value of resistors 86 and 88, and capacitor 90. In the illustrated embodiment, the resistors 86 and 88 are selected at approximately 510K ohms and 1 M ohms, respectively and the capacitor 90 at approximately 0.0082MFD to give a time period of about 0.0096 seconds, such that the counter output period is approximately 63 seconds. Accordingly, a clock of about one minute in duration is established. Pin 5 of counter 84 is tied high to disable the auto reset mode and pin 10 is tied high to enable the recycle mode. Pin 9 of counter 84 is tied high to make the initial output a logic one or high state after reset.

The control logic signal output at pin 8 of the timer/counter circuit 84 is fed to the clock inputs of a pair of four-stage up/down counters 92, 94 which are cascaded together and have their respective mode pins tied to logic low or zero to select the decimal mode and down counter mode, respectively. The Q1 and Q2 outputs of the second counter 94 are coupled with both inputs of a two-input OR gate 96 whose output feeds the control input 62 at the base electrode of transistor 66 through a current limiting resistor 98. Accordingly, during the time period when these Q1 and Q2 outputs of counter 94 are at a logic one or high state, the triac 78 will be in a conductive state, keeping the heater elements 40 energized. Since the timing pulses from the timer/counter are approximately 60 seconds in length, this time period is approximately 41 minutes. However, as will be seen presently, an entire heating cycle lasts approximately 60 minutes, with the additional 19 minutes being allowed for the containers 22 to cool down before the operator removes them.

In accordance with the further feature of the preferred embodiment illustrated herein, the control circuit further includes a cover sensor to determine whether the cover 16 is open or closed. In the illustrated embodiment, a Hall effect transistor switch 98, preferably of the type ULN3040T is utilized. This sensor element 98 is mounted in a suitable position (not shown) to sense the proximity of a magnet member 100 mounted in the cover 16 (see FIGS. 1 and 2). The Hall effect switch is an open-collector output device. Hence, the output is high or a logic one when the magnet is away from the Hall effect switch, that is, when the cover is open and the output is a logic zero or low when the magnet is near the Hall effect switch, that is, when the cover is closed. A pull-up resistor 102 is coupled with the collector electrode of the Hall effect transistor 98.

This collector electrode is also coupled to one input of a reset circuit 104 for resetting the timer/counter circuit, that is, resetting the master reset (MR) of timer/counter 84 to zero and presetting the down counters 92, 94 to a count of 60. The reset circuit is coupled to respond to powering up of the unit and resultant energization of a positive 5-volt supply voltage. Accordingly, a capacitor 106, a resistor 108 and a diode 110 are coupled to the positive voltage supply and the junction of these three elements is in turn coupled to one input of a two-input OR gate 112, the other input of which is coupled to the collector of the Hall effect transistor 98. On power up, the capacitor 106 is a short and causes the output of gate 112 to be high which will cause the above-noted resetting of the timer/counter 84 and the two down counters 92, 94. In about 40 milliseconds capacitor 106 charges up to the switching voltage of gate 112 the power on reset pulse ceases. Hence, if the power should go off at any time during the heating cycle, the cycle will be automatically restarted when the power is reapplied since this power reset circuit will be re-activated. The cover sensor 19 also acts by way of gate 112; to activate circuit 84 to the reset state and to reset the two digit down counter 92, 94 into its preset state of 60, when the cover is closed.

In accordance with another feature of the preferred embodiment illustrated herein, a temperature sensing circuit is also provided, and includes a temperature sensor element 120. The element 120 is preferably a negative temperature coefficient resistor (NTC) whose resistance decreases as the temperature increases. It will be seen that with decreasing resistance, the bias of Hall effect transistor 98 will eventually reach a point where the transistor will not conduct (less than about 0.6 volts of DC from base to emitter). With transistor 98 non-conducting, a further transistor 122 is also switched to the non-conducting state such that the collector voltage of transistor 122 goes to a logic one or high state. On the other hand, when the NTC cools down below the required temperature level transistor 122 again conducts and its collector voltage falls to a logic zero level. In this regard, any time the cover is open, the NTC ground end will be pulled up to 5 volts DC causing the collector of transistor 122 to go to a logic zero or low state. The remaining logic circuit portion of the control circuit and its operation will next be briefly described. As noted, upon power up the master reset (MR) of timer/counter 84 is active causing the preset counts 0, 6 to be loaded into counters 92 and 94, respectively, after the short time delay effected by resistor 124 and capacitor 126. Accordingly, if the cover remains open, the display count will be 60 and the ready lamp, preferably in the form of a green lighting emitting diode (LED) 130 will remain off. Up to six containers 22 may then be loaded into the receptacles 20 and the cover closed. Closing the cover- allows the timer/counter to begin generating timing pulses and the down counters to begin counting down from 60, to effect the above-noted cycle of 41 minutes of heating and 19 minutes of cooling down, whereupon the ready lamp 130 is lit.

In the illustrated embodiment, the display 50 consists of a pair of seven-segment display characters 140, 142. These displays are driven from the down counters 92, 94 by way of respective binary coded decimal to seven-segment decoder/display driver circuit components 144, 146, which in the illustrated embodiment preferably comprise components of the type generally designated MC14511B. The display characters 140 and 142 preferably comprise a light emitting diode (LED) type display members of the type generally designated HDSP-7303. Suitable intervening current resistors 148 and 150 are also utilized between the drivers and the respective display characters.

Briefly, the power supply circuit 160 comprises a 12 volt DC power supply utilizing a 60 cycle power transformer 162 having a 115 volt AC primary and a 10 volt (RMS) secondary. A diode bridge 164 is used to full wave rectify 10 volts RMS to a reservoir capacitor 166. A five-volt solid state voltage regulator 168, preferably of the type generally designed LM7805, is provided with a regulator output capacitor 170.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A disinfector apparatus for effecting heat disinfection by heating of a plurality of devices such as contact lenses, each of said plurality of devices being disposed in a quantity of liquid within a closed container, said apparatus comprising: a housing, a plurality of receptacles defined within said housing, each said receptacle being of a complementary shape for receiving a portion of one of said containers therewithin; heating means disposed for heating said receptacles to thereby heat respective containers disposed therein, and control circuit means for controlling a predetermined cycle of heating effected by said heating means; wherein said heating means comprises at least one electrically energizable heating element and wherein said control circuit means comprises controllable switching means coupled with said heating means and with a source of electrical power and having a control input, said controllable switching means being responsive to a control signal at said control input for alternatively making and breaking an electrical circuit between said power source and said heating means, and timer circuit means coupled with said control input for producing said control signal for causing energization of said heating means for a predetermined time duration; wherein said timer circuit means includes reset input means responsive to a reset signal for resetting the timer circuit means to restart said predetermined time duration of heating by said heating means; wherein said housing includes a selectively openable and closable cover member, and wherein said control circuit means further includes cover sensor means responsive to said cover portion being open and being closed, respectively, for continuously producing said reset signal until said cover portion is closed.

2. Apparatus according to claim 1, wherein each said receptacle is disposed at a predetermined angular offset relative to vertical and horizontal directions when said housing is resting on a horizontal surface, to thereby hold each of said containers at a corresponding angular offset for facilitating heat transfer from said heating means to the liquid in each said container 3. Apparatus according to claim 2 wherein said angular offset is on the order of substantially 45 degrees.

4. Apparatus according to claim 2 wherein said heating means comprises at least one positive temperature coefficient element.

5. Apparatus according to claim 1 wherein said receptacles are oriented in at least one row in a side-by-side arrangement such that bottom wall portions thereof are aligned in co-planar arrangement and define a substantially planar undersurface, and wherein said heating means is mounted for heating each said planar undersurface.

6. Apparatus according to claim 5 and further including bracket means for mounting said heating means to said planar undersurface, said bracket means including means for facilitating substantially even heat distribution from the heating means to each said receptacle in the associated row.

7. Apparatus according to claim 1 wherein said receptacles are formed of a heat sinking material to further facilitate the transfer of heat from said heating means to said containers.

8. Apparatus according to claim 1 wherein said control circuit means further includes temperature sensing means responsive to the temperature of said receptacles for producing a corresponding temperature signal and indicator circuit means responsive to said temperature signal and to said timer circuit means for producing a corresponding indication when said predetermined cycle is completed.

9. Apparatus according to claim 8 wherein said temperature sensor means comprises at least one negative temperature coefficient element.

10. Apparatus according to claim 1 and further including time display means responsive to said timer circuit means for producing a corresponding time display.

11. Apparatus according to claim 10 wherein said time display means comprises down counter circuit means for displaying the time remaining of said predetermined cycle.

12. Apparatus according to claim 1 wherein said heating means comprises at least one positive temperature coefficient element.

13. Apparatus according to claim 1 wherein said control circuit means further includes temperature sensor means responsive to the temperature of said receptacles for producing a corresponding temperature signal and indicator circuit means responsive to said temperature signal and to said timer circuit means for producing a corresponding indication when said predetermined cycle is completed.

14. Apparatus according to claim 13 wherein said temperature sensor comprises a negative temperature coefficient element.

15. Apparatus according to claim 1 and further including time display means responsive to said timer circuit means for producing a corresponding time display.

16. Apparatus according to claim 15 wherein said time display means comprises down counter circuit means coupled to said timer circuit means for producing a display signal corresponding to the time remaining of said predetermined cycle and visual display means for displaying said time remaining in response to said down counter circuit means.

* * * * *